United States Patent [19]

Swindell et al.

[11] Patent Number: 5,543,411
[45] Date of Patent: Aug. 6, 1996

[54] HYDROXYLATED METABOLITES AND DERIVATIVES OF DOXAZOSIN AS ANTI-ATHEROSCLEROSIS AGENTS

[75] Inventors: Archie C. Swindell, Groton; Samuel S. Wong, Newtown, both of Conn.

[73] Assignee: Pfizer Inc., New York, N.Y.

[21] Appl. No.: 436,787

[22] Filed: May 8, 1995

Related U.S. Application Data

[63] Continuation of Ser. No. 116,431, Sep. 3, 1993, abandoned, which is a continuation of Ser. No. 861,714, Apr. 1, 1992, abandoned.

[51] Int. Cl.$^6$ .......................... A61K 31/495; A61K 31/50
[52] U.S. Cl. ............................................. 514/254; 514/824
[58] Field of Search ....................................... 514/254, 824

[56] References Cited

U.S. PATENT DOCUMENTS

| | | | |
|---|---|---|---|
| 4,188,390 | 2/1980 | Campbell | 424/251 |
| 4,758,569 | 7/1988 | Swindell | 514/254 |

FOREIGN PATENT DOCUMENTS

| | | |
|---|---|---|
| 271997 | 9/1986 | United Kingdom . |

OTHER PUBLICATIONS

Hansch et al., *J. Med. Chem.*, vol. 16, No. 11, pp. 1217–1222 (1973).

Goodman and Gilman's "The Pharmacological Basis of Therapeutics", 8th edition, edited by A. G. Gilman et al., Pergamon Press Inc., New York, 1990, chap. 1, pp. 13–14.

Lipinski, C., *Annual Reports in Medicinal Chemistry*, 21, chap. 27, pp. 283–291, 1986, Academic Press Inc., Dennis M. Bailey, Ed.

Ryffel et al., *Transplantation Proceedings*, vol. XX, No. 2, suppl. 2, pp. 575–584 (Apr. 1988).

Schlitt et al., *Transplantation Proceedings*, vol XIX, No. 5, pp. 4248–4251 (Oct., 1987).

*Primary Examiner*—Kimberly Jordan
*Attorney, Agent, or Firm*—Peter C. Richardson; Paul H. Ginsburg; Karen DeBenedictis

[57] ABSTRACT

This invention relates to the use of certain hydroxylated metabolites and derivatives of doxazosin and their pharmaceutically acceptable acid addition salts for retarding the development of atherosclerosis in a mammal. Such compounds are useful for reducing atherosclerotic plaque involvement and for retarding and reducing both lipid deposition fibrosis in the development of atherosclerotic plaques.

6 Claims, No Drawings

HYDROXYLATED METABOLITES AND DERIVATIVES OF DOXAZOSIN AS ANTI-ATHEROSCLEROSIS AGENTS

This is a continuation, of application Ser. No. 08/116, 431, filed on Sep. 3, 1993 now abandoned, which is a continuation under 37 CFR §1.60 of application Ser. No. 07/861,714, filed on Apr. 1, 1992, now abandoned.

BACKGROUND OF THE INVENTION

This invention relates to the use of certain hydroxylated metabolites and derivatives of doxazosin (4-amino-2-[4-(1, 4-benzodioxan-2-carbonyl)-piperazin-1-yl]-6,7- dimethoxyquinazoline), and their pharmaceutically acceptable acid addition salts for retarding the development of arterial disease in mammals, and, more specifically, for suppressing lipid deposition and fibrosis in the development of atherosclerotic plaques and thus reducing atherosclerotic plaque involvement in mammals.

Atherosclerosis, a disease of the arteries, is recognized to be the leading cause of death in the United States and Western Europe. The pathological sequence leading to atherosclerosis and occlusive heart disease has been described in detail by Ross and Glomset in New England Journal of Medicine 295, 369–377 (1976). The earliest stage in this sequence is the formation of "fatty streaks" (plaques) in the carotid, coronary and cerebral arteries and in the aorta. These, in turn, give rise to development of the "fibrous plaque", which consists of accumulated intimal smooth muscle cells laden with lipid and surrounded by extracellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscular spasm that characterize advanced atherosclerosis.

Statistical evidence suggests that hyperlipidemia and hypertension are primary risk factors in causing atherosclerosis. Treatment of atherosclerosis is, therefore, approached by attempts to control hypertension and hyperlipidemia by dietary or pharmacological means. Some success has been achieved in reducing the incidence and severity of atherosclerosis by strict adherence to a prudent diet, by lowering plasma lipids with drugs or with ileal bypass surgery and by lowering systemic blood pressure with diet or drugs. However, coronary heart disease remains a threat, even to individuals striving to control their risk factors. It has been speculated that every individual in the United States has some degree of atherosclerosis. This fact, along with the high associated mortality and the inadequacy of the present treatment methods, establishes the need for anti-atherosclerotic agents.

Doxazosin, its pharmaceutically acceptable acid addition salts and the use of doxazosin and such salts as regulators of the cardiovascular system, particularly in the treatment of hypertension, are referred to in U.S. Pat. No. 4,188,390, which is assigned in common with the present invention. The use of doxazosin as an antiatherosclerosis agent is referred to in U.S. Pat. No. 4,758,569, also assigned in common with the present invention.

Elliot et al., *Am. J. Cardio* 59, p. 78G–81G (1987), refer to two hydroxylated metabolites of doxazosin, in particular, the 5'-hydroxy and 6'-hydroxy metabolites. S. F. Campbell, in U.K. Patent Application No. 8605551, published as GB 271997A on Sep. 10, 1986 and assigned in common with the present invention, refers to the 5'-, 6'-, 7'- and 8'- hydroxy derivatives of doxazosin and their use in the treatment of hypertension and congestive heart failure.

Doxazosin, an inhibitor of α-adrengic receptors, is effective in treating hypertension and in lowering serum lipid levels in mammals. The present inventors have found that doxazosin inhibits aortic lipid infiltration and fibrosis in cholesterol fed rabbits and that this effect is independent of the lowering of blood pressure or serum lipid levels. This independent inhibition of aortic lipid infiltration and fibrosis by doxazosin is believed to be caused by the anti-oxidant properties of certain hydroxylated metabolites of doxazosin, and, in particular, the ability of these metabolites to inhibit the oxidative uptake of low density lipoproteins (LDL) by macrophages.

SUMMARY OF THE INVENTION

The present invention relates to a method of suppressing lipid deposition or fibrosis in the development of atherosclerotic lesions, or of reducing atherosclerotic lesions in a mammal having atherosclerosis, comprising administering to said mammal an atherosclerotic lesion reducing or fibrosis suppressing or lipid deposition suppressing affective amount of a compound of the formula

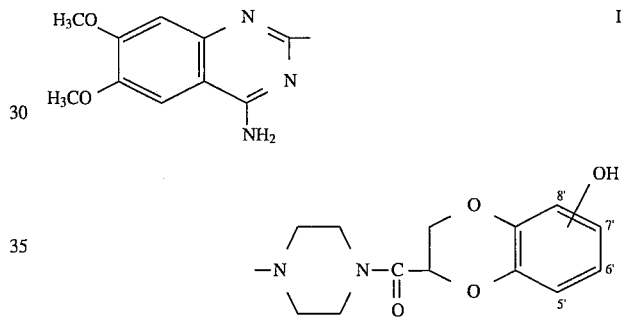

or a pharmaceutically acceptable salt thereof.

The terms "5'-hydroxy metabolite of doxazosin," "6'-hydroxy metabolite of doxazosin," "7'-hydroxy metabolite of doxazosin," and "8'-hydroxy metabolite of doxazosin," as used herein, refer to compounds of the formula I wherein the hydroxy group is attached to, respectively, the carbon atom labelled 5', 6', 7' and 8'.

A preferred embodiment of the present invention is the method described above wherein the 7'-hydroxy metabolite of doxazosin is administered.

The present invention also relates to pharmaceutical composition for suppressing lipid deposition or fibrosis in the development of atherosclerotic lesions, or reducing atherosclerotic lesions in a mammal having atherosclerosis, comprising an atherosclerotic lesion reducing or fibrosis suppressing or lipid deposition suppressing effective amount of compounds of the formula I, or a pharmaceutically acceptable salt thereof, and a pharmaceutically acceptable carrier.

DETAILED DESCRIPTION OF THE INVENTION

The compounds of the formula I and their pharmaceutically acceptable acid addition salts may be prepared as described in U.K. Patent application Publication No. GB2, 171,977A, referred to above, or by variations of the methods described therein that will be obvious to those skilled in the art. Such application is incorporated herein by reference in its entirety.

Examples of pharmaceutically acceptable acid addition salts of compounds of the formula I are the hydrochloride, hydrobromide, hydroiodide, nitrate, sulfate, bisulfate, phosphate, acid phosphate, acetate, lactate, citrate, acid citrate, tartrate, bitartrate, succinate, maleate, gluconate, methane sulfate, ethane sulfate, benzenesulfonate and p-toluene-sulfonate salts of such compounds.

In the treatment of atherosclerosis, the compounds of formula I and their pharmaceutically acceptable salts (i.e. the active compounds of this invention) can be administered via the oral or the parenteral, including transdermal, route. It is generally preferred to administer them orally. In general, these compounds are most desirably administered in doses ranging from about 1 mg up to about 32 mg per day, although variations will still necessarily occur depending upon the weight of the subject being treated. The appropriate dose for treatment of atherosclerosis with compounds of the formula I or their pharmaceutically acceptable salts will be readily determined by those skilled in the art of prescribing and/or administering such compounds. However, effective antihypertensive results are achieved with a dosage level that is in the range of from about 0.02 mg to about 0.60 mg/kg of body weight per day, with a preferred oral range in man being from about 0.15 to about 0.30 mg/kg per day. Nevertheless, variations may occur in this respect, depending upon the species of mammal being treated and its individual response to said medicament, as well as on the particular type of pharmaceutical formulation chosen in the time period and interval at which such administration is carried out. In some instances, dosage levels below the lower limit of the aforesaid range may be more than adequate, while in other cases still larger doses may be employed without causing any harmful or deleterious side effects to occur provided that such higher dose levels are first divided into several smaller doses that are to be administered throughout the day.

For purposes of oral administration, tablets containing excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tabletting purposes. Solid compositions of a similar type may also be employed as fillers in soft elastic and hard-filled gelatin capsules; preferred materials in this connection also include by way of example and not of limitation lactose or milk sugar as well as high molecular weight polyethylene glycols. When aqueous suspensions and/or elixirs are desired for oral administration, the essential active ingredient may be combined with various sweetening or flavoring agents, coloring matter or dyes, and, if so desired, emulsifying and/or suspending agents, together with diluents such as water, ethanol, propylene glycol, glycerin and various like combinations thereof.

Although the preferred mode of administration of the compounds of formula I or their pharmaceutically acceptable acid addition salts is oral, they may be administered parenterally as well.

For purposes of parenteral administration, solutions of these particular compounds in sesame or peanut oil or in aqueous propylene glycol may be employed, as well as sterile aqueous solutions of the corresponding water soluble acid addition salts previously enumerated. Such aqueous solutions should be suitably buffered if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous-earth or unglazed porcelain filter. Preferred filters of this type include the Berkefeld, the Chamberland and the Asbestos Disk-Metal Seitz filter, wherein the fluid is sucked into a sterile container with the aid of a suction pump. Needless to say, the necessary steps should be taken throughout the preparation of these injectable solutions to insure that the final products are obtained in a sterile condition.

The compounds of formula I and their pharmaceutically acceptable acid addition salts can also be administered transdermally. For purposes of transdermal administration, the dosage form of the particular compound may include, by way of example, solutions, lotions, ointments, creams, gels, suppositories, rate-limiting sustained release formulations and devices therefor. Such dosage forms comprise the particular compound and may include ethanol, water, penetration enhancers and inert carriers such as gel-producing materials, mineral oil, emulsifying agents, benzyl alcohol and the like. Specific transdermal flux enhancing compositions are referred to in pending U.S. patent application Ser. No. 07/759,705, which was filed on Sep. 11, 1991 and is assigned in common with this invention. Such application is incorporated herein by reference.

We claim:

1. A method of suppressing lipid deposition or fibrosis in the development of atherosclerotic lesions, or of reducing atherosclerotic lesions in a mammal having atherosclerosis, comprising administering to said mammal an atherosclerotic lesion reducing or fibrosis suppressing or lipid deposition suppressing effective amount of a compound having the formula

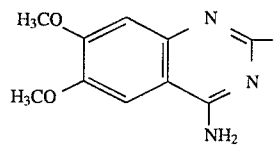

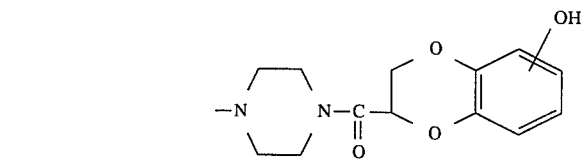

or a pharmaceutically acceptable acid addition salt thereof.

2. A method according to claim 1 wherein the 7'-hydroxy metabolite of doxazosin is administered.

3. A method according to claim 1 wherein the 6'-hydroxy metabolite of doxazosin is administered.

4. A method according to claim 1 wherein the compound of formula I or a pharmaceutically acceptable acid addition salt thereof is administered orally.

5. A method according to claim 1 wherein the compound of formula I or a pharmaceutically acceptable acid addition salt thereof is administered intraperitoneally.

6. A method according to claim 1 wherein the formula I or a pharmaceutically acceptable acid addition salt thereof is administered transdermally.

* * * * *